United States Patent [19]

Hochstein

[11] Patent Number: 4,960,996
[45] Date of Patent: Oct. 2, 1990

[54] RAIN SENSOR WITH REFERENCE CHANNEL

[76] Inventor: Peter A. Hochstein, 2966 River Valley Dr., Troy, Mich. 48098

[21] Appl. No.: 298,419

[22] Filed: Jan. 18, 1989

[51] Int. Cl.$^5$ ............................................. G01N 21/47
[52] U.S. Cl. ................................. 250/349; 15/250 C; 250/341; 318/DIG. 2
[58] Field of Search ................ 250/341, 349; 318/483, 318/DIG. 2, 480; 15/250 C; 356/448

[56] References Cited

U.S. PATENT DOCUMENTS

| | | | |
|---|---|---|---|
| 4,355,271 | 10/1982 | Noack | 250/341 |
| 4,365,896 | 12/1982 | Mihalow | 356/239 |
| 4,636,643 | 1/1987 | Nakamura et al. | 250/341 |
| 4,701,613 | 10/1987 | Watanabe et al. | 250/341 |
| 4,713,583 | 12/1987 | Hochstein | 15/250 A |
| 4,798,956 | 1/1989 | Hochstein | 250/341 |
| 4,859,867 | 8/1989 | Larson et al. | 15/250 C |
| 4,871,917 | 10/1989 | O'Farrell et al. | 250/339 |

Primary Examiner—Carolyn E. Fields
Attorney, Agent, or Firm—Reising, Ethington, Barnard, Perry & Milton

[57] ABSTRACT

A sensing assembly (10) for indicating when moisture or other particles have accumulated on a window (12) having inside (14) and outside (16) surfaces. The assembly includes an emitter (18) disposed on the inside surface (14) of the window (12) to emit infrared energy to the window (12). A detector (20) is disposed on the inside surface (14) to detect infrared energy from the window (12) on an egress axis. A reference detector (22) detects ambient light and emitter output which are parallel to the egress axis. A control circuit (24) receives the detected measurement level and reference level for comparison to actuate the wipers when rain or particles are on the window (12).

19 Claims, 2 Drawing Sheets

RAIN SENSOR WITH REFERENCE CHANNEL

TECHNICAL FIELD

This invention relates to electro-optical sensors for sensing radiant energy, and more specifically, sensors for sensing moisture on a window by reflecting radiant energy.

BACKGROUND OF THE INVENTION

Automatic rain sensors for controlling the windshield wipers on vehicles have employed optical sensors using infrared emitters and detectors to determine whether moisture is present on the windshield surface. Optical rain sensors can be adapted to any windshield without the need for special glass processing.

One such optical sensor is disclosed in U.S. Ser. No. 073,496 filed July 15, 1987, now U.S. Pat. No. 4,798,956, in the name of the inventor named herein. The sensor assembly is adapted to a window having inside and outside surfaces defining a thickness T and of a material having an index of refraction n. The assembly utilizes an emitter for emitting radiant energy toward the window at an incident angle Z relative to the inside surface and a detector for detecting radiant energy from the window at a reflection angle relative to the inside surface and equal to the incident angle Z. The emitter and detector are spaced a distance apart D on the inside surface of the window to compensate for refraction at the unmatched index plane. The distance D is determined by the following equation:

$$D = 2\, T\, \cos Z\, (n^2 - \cos^2 Z)^{-\frac{1}{2}}$$

The detector includes a collimator and infrared filter to eliminate the effects of extraneous radiant energy.

This assembly does not compensate for reduction in infrared emission from the emitter LED with increasing ambient temperature nor the partial reduction in photosensor sensitivity by high ambient light levels causing erroneous operation. Careful filtering of the photosensor cell to exclude all wavelengths but those emitted by the pulsed LED IR source does limit the sensitivity of the system to sunlight, however, certain lighting conditions which may cause a sun reflection or glint from car or road surfaces can still induce a detector overload resulting in an erroneous wipe signal.

Use of a reference channel has been utilized for sensing change in emitter output due to temperature or age. One such system is disclosed is U.S. Pat. No. 4,355,271 issued Oct. 19, 1982 in the name of Noack. The system includes an emitter transmitting radiant energy toward the window and reflected to a detector for sensing moisture or particles on the window. A second detector senses the radiant output only of the emitter. The signal from the first detector is compared to the signal from the second detector to determine actuation of the wipers.

A problem with this type of system is that ambient light is not accounted for which can interfere giving inaccurate results. Incident sunlight falling on the photodetector would easily saturate the sensor rendering the assembly useless.

SUMMARY OF THE INVENTION AND ADVANTAGES

The invention is a sensing assembly for indicating when moisture or other particles have accumulated on a window having inside and outside surfaces. The assembly comprises emitter means for disposition on the inside of the window to emit radiant energy to the window on an ingress axis, detector means for disposition on the inside of the window to detect radiant energy from the window on an egress axis emitted by said emitter means, and reference detector means for disposition on the window to detect the magnitude of ambient light and the radiant energy.

The advantages include the ability to sense ambient light and emitter output for compensation in the control circuit.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
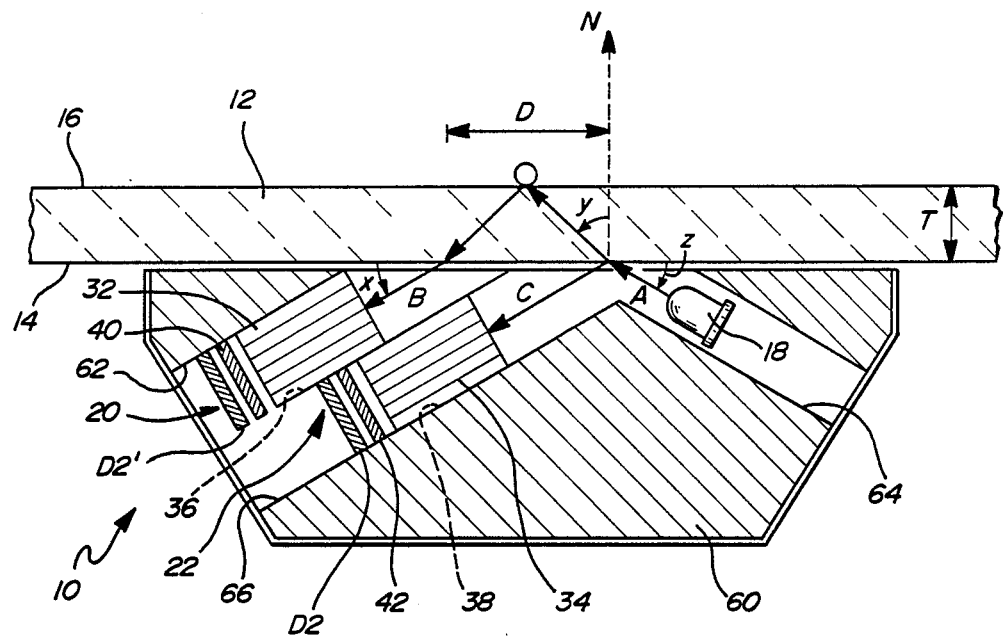
FIG. 1 is a partially broken away perspective view of the subject invention.

A sensing assembly for indicating when moisture or other particles have accumulated on a window 12 having inside 14 and outside 16 surfaces is generally shown at 10 in FIG. 1. The assembly 10 includes emitter means 18 for disposition on the inside of the window 12 to emit radiant energy toward the window 12 and detector means 20 for disposition on the inside of the window 12 to detect radiant energy from the window 12. Reference means 22 is also disposed on the inside surface 14 of the window 12 in the preferred embodiment to detect ambient light and the radiant energy from the emitter means 18.

The emitter means 18 and the detector means 20, without a reference channel is disclosed in U.S. Ser. No. 073,496 filed July 15, 1987. The assembly 10 is applied to the windshield of a vehicle, more particularly an automobile. Infrared energy is preferably used in automotive application to compensate for surrounding light interference. Commercially available infrared emitters emit energy peaking at approximately 940 nm while solar radiant energy peaks at approximately 500 nm. The following description makes reference to infrared energy, but it is to be understood that other radiant energy could be used depending on the application.

The emitter means 18 is positioned to emit pulses of radiant or infrared energy toward the window 12 on an ingress axis A. Due to the index of refraction n of air and glass, the positioning of the emitter means 18 and detector means 20 becomes important, as discussed subsequently. The infrared energy is transmitted through the window 12 and reflects off the outside surface 16 thereof and back through the window 12 to the detector means 20. If water is present on the glass, less energy will be reflected to the detector means 20, if dirt or other particles are present, more energy will be reflected back to the detector means 20. The detector means 20 senses radiant energy from the window 12 on an egress axis B. The magnitude of the detected radiant energy will comprise the reflected infrared energy and a portion of ambient light. The magnitude of the detected energy will therefore depend on the magnitude of incident light from the emitter means 18 and ambient light.

The reference means 22 receives radiant energy on a reference axis C substantially parallel with the egress axis B to detect the amount of radiant energy impinging thereon. More specifically, the reference means 22 is disposed on the inside surface 14 of the window 12 to detect the magnitude of ambient light and reflected radiant energy. By using the reference means 22, the assembly 10 is able to compensate for changes in ambient light and the output of the emitter means 18.

The assembly 10 includes control means 24 which receives a measurement signal from the detector means 20 and the reference signal from the reference means 22 for comparing the signals to produce a wipe signal activating the vehicle wipers when moisture or other particles have accumulated on the window 12. The control means 24 includes a measurement channel 26 for receiving the measurement signal producing a measurement level and a reference channel 28 for receiving the reference signal producing a reference level. The comparator means 30 receives the reference level and the measurement level and produces the wipe signal when the measured level moves past the reference level.

The reference means 22 and detector means 20 includes limiting means 32, 34 for limiting the field of view of radiant energy from the window 12 entering the reference means 22 and detector means 20 by allowing to pass radiant energy substantially parallel with the reference axis C and egress axis B within the field of view. The limiting means 32, 34 comprises a first collimator 32 having a first end adjacent the window 12 and a second end containing the detector means 20, and a second collimator 34 having a first end adjacent the window 12 and a second end containing the reference detector means 20. The collimators 32, 34 include absorbing means 36, 38 on their interior surfaces thereof for absorbing non-parallel radiant energy to prevent the detection thereof. A filter means 40, 42 is included in each of the reference means 22 and the detector means 20 to receive parallel radiant energy filtering out radiant energy which fall outside a predetermined wavelengths.

Generally, the emitter means 18 includes pulsing means 44 for emitting radiant energy, or more specifically infrared energy, toward the window 12. The pulsing means 44 may be a commercially available infrared emitter, which includes an infrared emitter diode D1. The pulsing means 44 may be connected to a voltage source 46 such as the battery of the vehicle. A voltage regulator 48 receives this voltage and sends a regulated voltage to an astable pulse generator 50. The astable pulse generator 50 pulses the emitter to produce an output of pulsed radiant energy.

Figure 2:
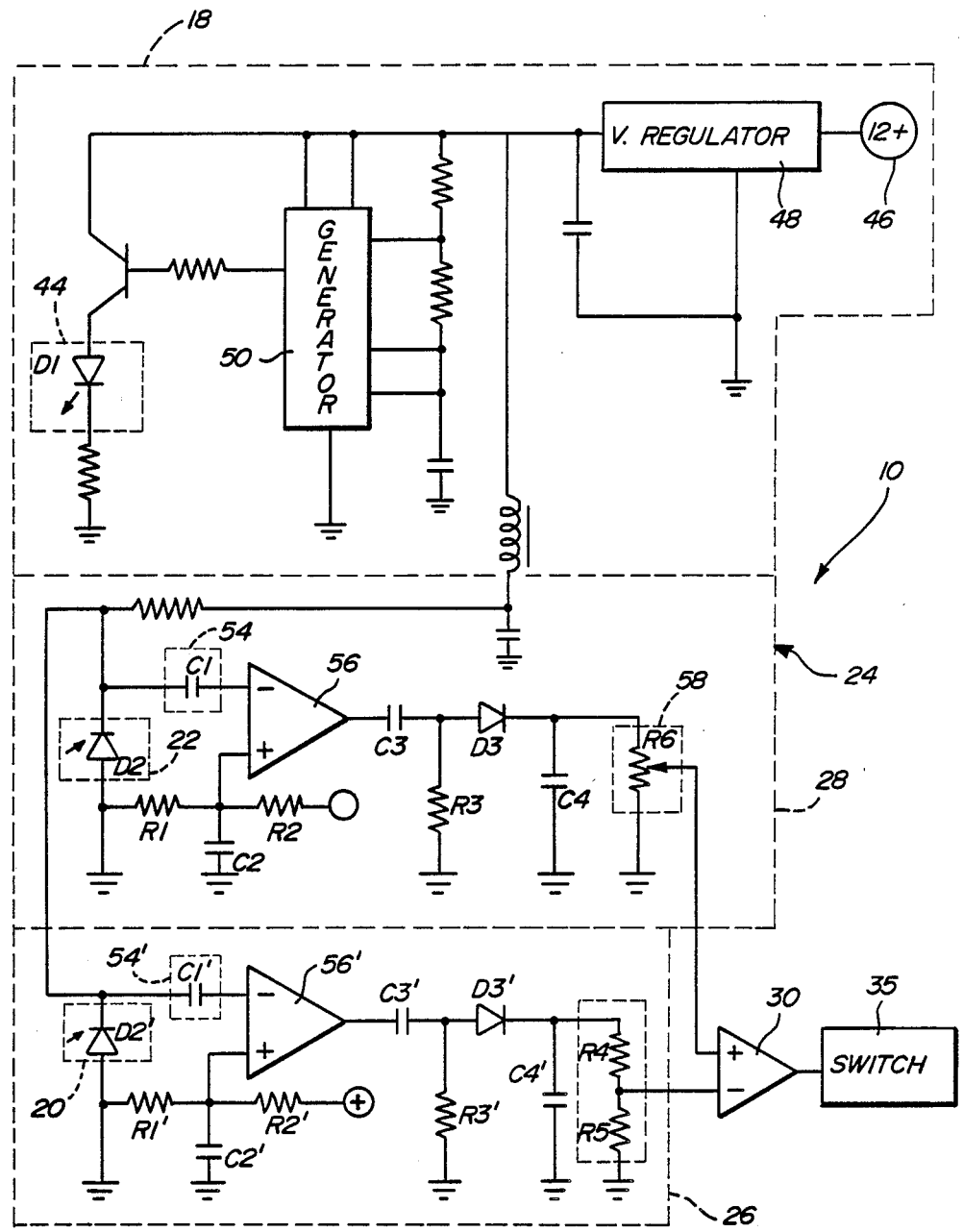
FIG. 2 is a schematic of the control means 24 of the subject invention.

As illustrated in FIG. 2, the control means 24 includes the reference channel 28 and the measurement channel 26 for establishing a measurement level and reference level, and the comparator means 30 for receiving and comparing the levels to produce the wipe signal. The circuitry for the detector channel 26 and reference channel 28 are the same up to the comparator means 30. The detector channel 26 has reference numbers primed (') and correspond to like numbers in the reference channel 28.

The detector 26 and reference 28 channels include an infrared light sensitive means D2, D2' responsive to light energy for producing an electrical signal. The infrared light sensitive means is a filtered photodiode D2,D2' which receives the infrared pulses through the limiting means 32, 34, or collimator. The photodiode D2,D2' is typically sensitive to visible light as well as infrared energy. The control means 24 includes coupling means 54, 54' for ac coupling the electrical signal to an amplifier means 56, 56'. The amplifier means 56, 56' linearly amplifies the magnitude of the electrical signal producing an amplified signal. The photodiode D2,D2' is reversed biased, and ac coupled by the coupling means 54, 54', which is a capacitor C1, C1', to the amplifier means 56, 56' and which is and operational amplifier having a nominal ac gain of 15. The non-inverting pin of the op-amp 56 56' includes voltage divider resistors R1, R2, R1', R2' connected between ground an positive voltage source 46, and a capacitor C2, C2' connected to ground and the non-inverting pin. The detected electrical signal of the measurement channel 26 is proportional to the amount of moisture or water droplets on the outside surface 16 of the window 12 and the detected electrical signal of the reference channel 28 is proportional to the amount of ambient light and emitter output. When dry, the outside surface 16 of the window 12 reflects a relatively larger proportion of the illuminating incident infrared energy then when the outside surface 16 has water present effecting the measurement level only. The electrical signals are converted to a proportional dc level (reference level and measurement level) by the rectifying network consisting of coupling capacitor C3, C3', resistor R3, R3', diode D3, D3', capacitor C4, C4' and resistive network 58, 58'. The resistive network 58' of the measurement channel 26 includes a voltage divider comprising resistors R4, R5 connecting the measurement level to the inverting input of the comparator means 30.

The comparator means 30 receives the measurement level and compares it to the reference level to determine the amount of moisture or other particles on the window 12. The comparator means 30 includes an operational amplifier. The comparator means 30 produces a wipe signal if the measurement level falls below a given threshold established by the set point adjustment or the variable resistor R6 which produces the reference level. The reference channel 28 allows for adaptive control of the setpoint to compensate for environmental variables. The use of this reference channel 28 to derive a setpoint can compensate for changes in infrared illumination due to changes in emitter output due to temperature and/or aging. Further, compensation is provided for changes in circuit component performance, and additional compensation may be achieved for the intrusion of ambient light which may adversely affect the sensitivity of the detector means 20. A switch 35 is responsive to the comparator means 30 to turn on and off the wipers.

As disclosed in U.S. Ser. No. 073,496, positioning of the emitter means 18 and the detector means 20 is critical. The emitter means 18 produces radiant energy which is directed or emitted toward the window 12 at an incident angle Z and refracted at an angle Y (angle from the normal N) at the air-inside window 12 interface. The refracted radiant energy is passed through the window 12 and is then reflected off the air-outside window 12 surface back through the window 12 and out the air-inside window 12 surface at which point it is refracted and angled away from the window 12 at a reflection angle X equal to that of the incident angle Z. The inside 14 and outside 16 surfaces of the window 12 define a thickness T. The window 12 is of a material having an index of refraction n; the index of refraction n also varies with the wavelength of the radiant energy.

Support means 60 supports the emitter means 18 and the detector means 20 such that the point I of intersection of the ingress axis A with the inside surface 14 of the window 12 from the point E of intersection of the egress axis B with the inside surface 14 of the window 12 is a predetermined distance D. The emitter means 18 and detector means 20 have an effective beam diameter of radiant energy. Between the central point where these diameters intersect on the inside window 12 surface. The following formula was developed to determine the distance between the intersection of the ingress axis A of the emitter means 18 with the inside surface 14 of the window 12 and the intersection of the egress axis B of the detector means 20 with the inside surface 14 of the window 12 which is dependent of the index of refraction n n, the incident or reflection angle, and the thickness of the glass T:

$$D = 2T \cos Z (n^2 - \cos^2 Z)^{-\frac{1}{2}}$$

The support means 60 supports the emitter means 18 and the detector means 20 at the predetermined distance D and angles X, Z configuration. The support means 60 includes a detector holder means 62 directed toward the window 12 at the reflection angle X directed below the horizon. The support means 60 includes emitter holder means 64 for securing the emitter means 18 directed toward the window 12 at the incident angle Z equal to the reflection angle X. The support means 60 includes reference holder means 66 to support the reference detector at the reflection angle X to receive reflected light off the inside surface 14 of the window 12 from the emitter means 18. The emitter means 18 transmits infrared energy toward the window 12 and a portion of the radiant energy is reflected off the inside surface 14 on a reflection axis C without entering the window 12 which is received by the reference means 22.

The emitter holder means 64, the detector holder means 62 and reference holder means 66 are tubular in shape and either circular or rectangular in cross-section having an outer diameter or aperture of the effective beam diameter of radiant energy centered about the ingress A and egress B and reflection C axes, respectively. The distance between the intersection of the central point of the two holder means or ingress A and egress B axes, with the inside surface 14 of the window 12 is set by the calculated predetermined distance D.

The tubular emitter holder means 64 and the tubular detector holder means 62 partially overlap at their outside apertures at the plane of the window 12. Therefore, the support means 60 includes blocking means 68 at the location of the partial overlapping of the two holder means adjacent the window 12 for blocking radiant energy from the emitter means 18 to the detector means 20 reflected off the inside surface 14 of the window 12. The support means 60 encloses the emitter means 18 and detector means 20. The support means 60 includes openings adjacent the window 12 for allowing the infrared energy to pass from the emitter means 18 and for allowing the light energy to be received by the detector means 20 and reference means 22. Location of placement and adhesion means is disclosed in U.S. Ser. No. 073,496.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A sensing assembly for indicating when moisture or other particles have accumulated on a window having inside and outside surfaces, said assembly comprising; emitter means (18) for disposition on the inside of the window (12) to emit radiant energy to the window (12) on an ingress axis (A), detector means (20) for disposition on the inside of the window (12) to detect radiant energy emitted by said emitter means (18) and received along an egress axis (B) extending from the window (12), and characterized by including reference detector means (22) for disposition on the window (12) to receive radiant energy directed by the window (12) and emitted by said emitter means (18) and to detect the magnitude of said radiant energy.

2. An assembly as set forth in claim 1 further characterized by including control means (24) for receiving a measured signal from said detector means (20) and a reference signal from said reference detector means (22) for comparing said signals to produce a wipe signal.

3. An assembly as set forth in claim 2 further characterized by said reference detector means (22) receiving radiant energy on a reference axis (C) parallel to said egress axis (B).

4. An assembly as set forth in claim 3 further characterized by including limiting means (32, 34) for limiting the field of view of radiant energy from the window (12) entering said reference detector means (22) by allowing to pass radiant energy substantially parallel with the reference axis (C) within the field of view.

5. An assembly as set forth in claim 4 further characterized by said limiting means (32, 34) comprising a collimator having a first end adjacent the window (12) and a second end containing said reference detector means (22).

6. An assembly as set forth in claim 5 further characterized by said collimator including absorbing means (36) on the interior surface thereof for absorbing non-parallel radiant energy to prevent the detection thereof.

7. An assembly as set forth in claim 4 further characterized by including filter means (40) for receiving said substantially parallel radiant energy to filter out radiant energy which falls outside a predetermined wavelength band.

8. An assembly as set forth in claims 7 or 2 further characterized by said control means (24) including a measurement channel (26) for receiving said measured signal to produce a measured level and a reference channel (28) for receiving said reference signal to produce a reference level.

9. An assembly as set forth in claim 8 further characterized by said control means (24) including comparator means (30) for receiving said reference level and said measured level and producing an actuating signal when said measured level moves past said reference level.

10. An assembly as set forth in claim 1 further characterized by said reference detector means (22) receiving radiant energy reflected off the inside surface of the window (12).

11. A sensing assembly for indicating when moisture or other particles have accumulated on a window having inside and outside surfaces, said assembly comprising; emitter means (18) for disposition on the inside of the window (12) to emit radiant energy to the window (12) on an ingress axis (A), detector means (20) for disposition on the inside of the window (12) to detect radiant energy emitted by said emitter means (18) and received on an egress axis (B) extending from the window (12), and characterized by reference detector means (22) for receiving radiant energy on a reference axis (C) substantially parallel with said egress axis (B) to detect the amount of radiant energy impinging thereon.

12. An assembly as set forth in claim 11 further characterized by including control means (24) for receiving a measured signal from said detector means (20) and a reference signal from said reference detector means (22) for comparing said signals to produce a wipe signal for activating vehicle wipers when moisture or other particles have accumulated on the window (12).

13. An assembly as set forth in claim 12 further characterized by including limiting means (32, 34) for limiting the field of view of radiant energy from the window (12) entering said reference detector means (22) by allowing to pass radiant energy substantially parallel with the reference axis (C) within the field of view.

14. An assembly as set forth in claim 13 further characterized by including filter means (40, 42) for receiving said substantially parallel radiant energy to filter out radiant energy which falls outside a predetermined wavelength band.

15. An assembly as set forth in claim 14 further characterized by said control means (24) including a measurement channel (26) for receiving said measured signal to produce a measured level and a reference channel (28) for receiving said reference signal to produce a reference level.

16. An assembly as set forth in claim 15 further characterized by said control means (24) including comparator means (30) for receiving said reference level and said measured level and producing an actuating signal when said measured level moves past said reference level.

17. A sensing assembly for indicating when moisture or other particles have accumulated on a window having inside and outside surfaces, said assembly comprising; emitter means (18) for disposition on the inside of the window (12) to emit radiant energy to the window (12) on an ingress axis (A), detector means (20) for disposition on the inside of the window (12) to detect radiant energy emitted by said emitter means (18) and received along an egress axis (B) extending from the window (12), reference detector means (22) for disposition on the window (12) to detect the magnitude of ambient light entering through the window (12) substantially from the same direction as ambient light entering said detector means (20).

18. An assembly as set forth in claim 17 further characterized by said reference detector means (22) receiving ambient light on a reference axis (C) substantially parallel to said egress axis (B).

19. A support housing assembly for a rain sensor for disposition on a window having an emitter for emitting radiant energy toward a window and a detector for sensing reflected radiant energy from the window on an egress axis and a reference detector for sensing ambient light and radiant energy parallel to the egress axis, said assembly comprising: support housing for disposition on the inside surface (14) of a window (12), said support housing comprising emitter holder means (64) for holding an emitter such that when the assembly is disposed on the window, the emitter is directed toward the window (12), detector holder means (62) for supporting a measurement detector on an egress axis (B), and characterized by reference holder means for supporting a reference detector parallel to said egress axis (B).

* * * * *